United States Patent [19]
Oddo et al.

[11] Patent Number: 5,370,799
[45] Date of Patent: Dec. 6, 1994

[54] ELEVATED TEMPERATURE-PRESSURE FLOW SIMULATOR

[75] Inventors: John E. Oddo, Houston; Mason B. Tomson, West University Place, both of Tex.

[73] Assignee: Gas Research Institute, Chicago, Ill.

[21] Appl. No.: 33,634

[22] Filed: Mar. 16, 1993

[51] Int. Cl.$^5$ .................... G02F 1/00; G01N 37/00
[52] U.S. Cl. ................... 210/696; 73/61.62; 73/865.6; 137/7; 137/88; 166/311; 210/749; 210/741; 366/145; 366/152; 417/5; 436/6; 436/25
[58] Field of Search ............... 364/502, 510; 73/61.62; 417/5; 422/81, 82.12, 82.13, 93, 98, 109, 112; 436/6, 25, 28, 29, 52; 137/3, 7, 14, 88, 93; 210/696, 698, 699, 741, 742, 90, 93, 134, 143, 198.1, 205

[56] References Cited

U.S. PATENT DOCUMENTS

| | | | |
|---|---|---|---|
| Re. 33,468 | 12/1990 | Brindak | 73/61.62 |
| 3,470,735 | 10/1969 | Bradley | 73/61.62 |
| 4,304,122 | 12/1981 | Tentor | 73/865.6 |
| 4,306,581 | 12/1981 | Alandt | 137/93 |
| 4,426,880 | 1/1984 | Walters et al. | 75/61.62 |
| 4,460,008 | 7/1984 | O'Leary et al. | 137/93 |
| 4,538,452 | 9/1985 | Hrvojic | 73/865.6 |
| 4,648,043 | 3/1987 | O'Leary | 364/510 |
| 4,705,503 | 11/1987 | Dorman et al. | 604/65 |
| 4,714,545 | 12/1987 | Bente et al. | 210/101 |
| 4,863,571 | 9/1989 | Chambaere | 204/404 |
| 4,945,939 | 8/1990 | Maxwell et al. | 137/93 |
| 5,018,577 | 5/1991 | Pardue et al. | 210/699 |
| 5,034,190 | 7/1991 | Economy et al. | 422/53 |
| 5,234,587 | 8/1993 | Allington et al. | 210/101 |
| 5,253,981 | 10/1993 | Yang et al. | 417/5 |
| 5,263,541 | 11/1993 | Barthrope et al. | 210/747 |
| 5,291,950 | 3/1994 | Grebennikov | 166/312 |
| 5,302,297 | 4/1994 | Barthrope | 210/747 |

OTHER PUBLICATIONS

"Instrumentation and Automation Systems for Waterworks", Katsumi Kawabe et al., published in Toshiba Review, vol. No. 133, May-Jun. 1981 issue.

J. E. Oddo and M. B. Tomson, Why Scale Forms in Oil Field and Methods to Predict It (Title changed for publication to Improvements on the Oddo-Tomson Saturation Indices for the Prediction of Common Oil Field Scales), J. Petr. Eng., (1993).

J. E. Oddo, J. P. Smith, and M. B. Tomson, Analysis of and Solutions to the $CaCO_3$ and $CaSO_4$ Scaling Problems Encountered in Wells Offshore Indonesia, SPE 22782, Soc. Petr. Engr. 66th Ann. Tech. Conf., Dallas, Tex., (Oct. 6-9, 1991).

J. E. Oddo, C. Stiz, I. Ortiz, D. Linz, A. Lawrence, A. T. Kan and M. B. Tomson, Naturally Occuring Radioactive Materials (NORM) Scale Formation -A Case study of the Chemistry, Prediction, Remediation and Treatment in Wells of the Antrim Gas Fields Near Gaylord Mich., SPE/EPA Exploration and Production Environmental Conference, San Antonio, Tex., Mar. 7-10, 1993.

Primary Examiner—Joseph W. Drodge
Attorney, Agent, or Firm—Speckman, Pauley & Fejer

[57] ABSTRACT

An apparatus and process for simulation of field fluid flow conditions under elevated temperature and pressure conditions of oil and gas production, refining, cooling towers, desalinization. The process involves evaluating inhibitor action in reduction of a specified chemical reaction under simulated field aqueous flow conditions by forming first and second aqueous flow streams having a preset concentration of anions and cations, respectively, for the specified chemical reaction with at least one of these streams having a concentration of the inhibitor to inhibit the specified chemical reaction. These streams are combined to form a single process stream where the specified chemical reaction may take place. The process is repeated with successive reductions in inhibitor until detecting the specified chemical reaction in the process stream. The system of this invention is useful for study of problems of scaling, corrosion and other fluid-solid reactions and evaluation of inhibitors therefore, particularly with respect to $BASO_4$, whose solubility decreases with low temperatures and pressures and which frequently include substituted naturally occurring radioactive materials.

17 Claims, 1 Drawing Sheet

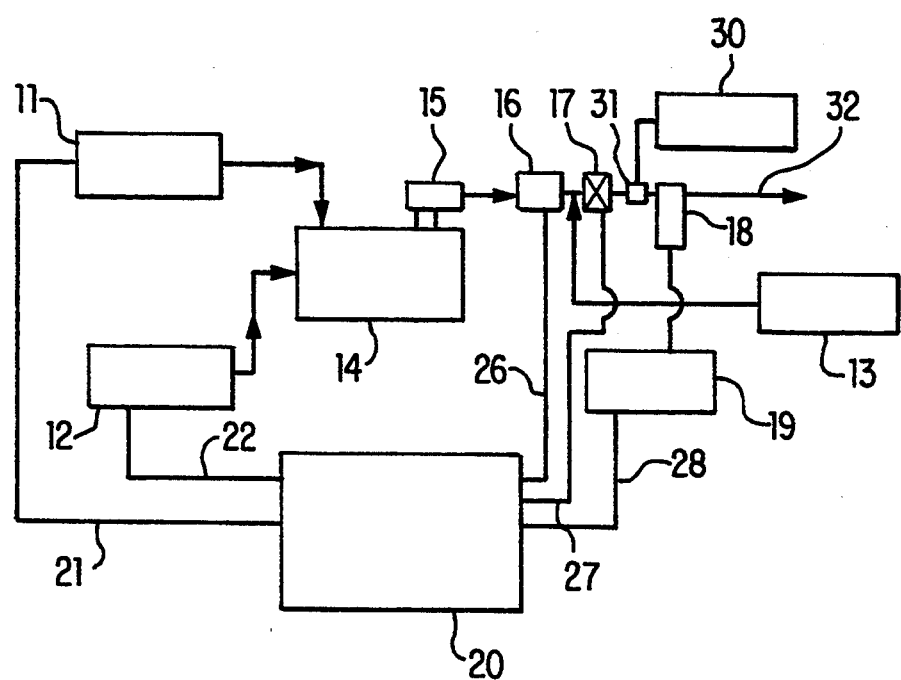

ELEVATED TEMPERATURE-PRESSURE FLOW SIMULATOR

BACKGROUND OF THE INVENTION

1. Field of the Invention

This invention relates to an apparatus and process for simulating field fluid flow conditions under elevated temperature and pressure for evaluation of precipitation, corrosion, and other fluid-solid reactions. The system of this invention may be used to study problems encountered in gas and oil production, refining, cooling towers, desalination and to evaluate chemicals for their effectiveness in reduction of these problems.

2. Description of Related Art

Electronically controlled proportioning pumps for varied mixing of a plurality of liquids providing a smooth composition gradient in the output flow of uniform velocity and pressure are taught by U.S. Pat. No. 4,714,545. The output flow may pass through a sample injection valve and combined output flow with sample delivered to an analytical instrument, such as a chromatograph.

There are a wide variety of systems for sensing and adding desired chemical in a bypass line of a flowing liquid: U.S. Pat. No. 4,945,939 teaches a computerized pH control system to control the pH in a reservoir system by monitoring a side recirculating stream for pH changes from preset tolerance and injecting pH affecting liquid in the side stream downstream from the monitoring tap for passage to the reservoir; U.S. Pat. No. 4,306,581 teaches a chemical concentration control system for a fluid circulator having an independent diverter and chemical addition line downstream from the circulator and returning to the fluid reservoir and within the diverter line a flow-through conductivity cell continuously monitors the chemical composition and at a preset value activates a solenoid valve allowing concentrated chemical to be aspirated into the line and passed to the solution tank until the desired concentration is restored and the solenoid valve deactivated and closed; A computer controlled system for introduction of chemicals into a water treatment system taught by U.S. Pat. No. 4,648,043 has a shunt line having a first sensor, a downstream injector for adding a second fluid, and a downstream second sensor, the sensors signalling a computer which controls the injector in accordance with preset parameters.

U.S. Pat. No. 4,460,008 teaches a cooling water tower control system which senses tower water and make-up water conductivity and utilizes these readings to establish an indexing factor for adjusting the trip point.

U.S. Pat. No. 4,705,503 teaches a catheter having an internal metabolite sensor downstream from a semipermeable region where dynamic equilibrium is attained between in-vivo external metabolite and higher concentration metabolite in the infusate. Changing metabolite concentration controls a chemical valve providing codelivery of a drug.

U.S. Pat. No. 5,034,190 teaches an apparatus and process for accelerated corrosion testing of nickel alloys by subjecting a mechanically stressed sample to a high temperature mixture of steam and hydrogen. Hydrogen is injected into the pressurized vessel through a selective hydrogen permeable membrane.

U.S. Pat. No. 4,863,571 teaches simulating and electrochemically determining corrosive behavior of an electrical conducting element embedded in a polymer by using the element as a working electrode of an electrochemical cell having a viscous electrolyte containing at least one corrosive substance. The electrode may be pretreated with a corrosion inhibitor to evaluate that inhibitor.

Submersible pump flow simulations for $CaCO_3$ scaling and effectiveness of scale inhibitors therefore has been described in J. E. Oddo, J. P. Smith, and M. B. Tomson, Analysis of and Solutions to the $CaCO_3$ and $CaSO_4$ Scaling Problems Encountered in Wells Offshore Indonesia, SPE 22782, Soc. Petr. Engr. 66th Ann. Tech. Conf., Dallas, Tex., (Oct. 6–9, 1991). The simulations described were only $CaCO_3$ scalings which were achieved by raising the temperature and monitored by pH change. Simulations were restricted to certain carbonate chemistries because in most instances carbonate scaling would occur in the container without inhibitor before the test began. Sulfate scales could not be detected by the apparatus shown in this article since they do not cause a pH change in water under most desired conditions of simulation.

SUMMARY OF THE INVENTION

Scale, corrosion and fouling in energy production equipment used in gas, oil or geothermal/geopressured water production are serious and costly problems which occur in the high temperature, pressure and ionic strength conditions of the production environment. To study and evaluate controls for these systems, it is important to have a laboratory flow simulator which accurately provides simulation of these production conditions. Surface discharge of brines has drawn recent attention since it has been found that water from some oil fields have radiation levels considerably higher than those allowed for discharge from nuclear power plants. Naturally occurring radioactive materials (NORM), particularly long lived radium and thorium, are common constituents of sediments of the earth's crust. Radium commonly substitutes into $BaSO_4$ causing the scale to be radioactive and presents a potential environmental problem which can be extremely expensive to alleviate and incur potential long term liabilities. With subsurface disposal of produced water, the low concentration of the dissolved species or radioactive radium is of low concern since the water is injected back into brine bearing aquifers in the sedimentary column. It does become important, however, that scale produced in the production system, particularly $BaSO_4$ scale concentrates and fixes radium in the well or on production equipment, which may then be classified as hazardous waste. This problem is further complicated by the fact that once formed, the $BaSO_4$ scale is most difficult to resolubilize and in many cases tubing must be drilled out or pulled and the scale physically removed, posing serious problems for producers. $BaSO_4$ scale also can seriously impact on field economics due to lost production and damaged equipment. Systematic methods to reliably control $BaSO_4$ scale formation, therefore, has the potential of saving the gas industry considerable money in reduced production, clean-up costs and future liabilities.

$BaSO_4$ scale occurs during gas and oil production in many places throughout the world, including the Michigan Basin, the Gulf Coast, Oklahoma and Alaska, in the United States. The scale is formed due to the inherent chemistry of the produced brine and the production conditions by commingling waters from different produced zones in the same well and by mixing incompatible waters in waterfloods. $BaSO_4$ has a very low solubility in water, which is demonstrated by the extreme likelihood of formation of the scale when a water containing very low concentrations of sulfate is mixed with a water containing relatively low concentrations of barium. Both pressure decreases and lowering of the temperature during production processes contribute to the likelihood of formation of $BaSO_4$ precipitation. Unlike $CaCO_3$ whose solubility increases with decreases in temperature, the solubility of $BaSO_4$ decreases significantly with decreases of temperature. Generally, the solubility of $BaSO_4$ is about half as much at 77° F. as it is at 203° F., regardless of salt concentration. Further, its solubility is about half as much at atmospheric pressure as it is at 6250 psi.

An effective scale control should prevent the formation of solid scale material with NORM, such as radium, remaining in solution at relatively low concentrations. However, there has been much disagreement in the literature as to the most effective chemical scale inhibitors to use and the dosage to use to prevent $BaSO_4$ scale. For accurate simulations, since $BaSO_4$ is more soluble at higher temperatures and pressures, solutions must be heated and pressurized for mixing, as opposed to prior inhibitor evaluations most of which have been performed at atmospheric pressure under static conditions.

It is, therefore, an object of this invention to provide an apparatus and process capable of reliable and accurate flow simulation utilizing controlled temperatures up to about 150° C. and pressures up to about 5000 psi to enable study and simulation of production equipment, particularly with respect to $BaSO_4$ scaling, but also including $FeCO_3$, $SrSO_4$, $CaSO_4$ and $CaCO_3$ scaling.

Another object of this invention is to separately heat and pressurize a plurality of salt solutions prior to mixing for evaluation of inhibitors for scale and corrosion under field simulated conditions.

These and other objects and advantages of this invention are achieved, in one embodiment, by a plurality of reactant high pressure pumps separately providing a plurality of pressurized aqueous field simulated streams, each containing an ionic concentration of one species required for the conduct of the desired simulated chemical reaction, with inhibitor to be evaluated initially present in at least one of the streams in an amount at least sufficient to effectively prevent the desired simulated chemical reaction, to a heater and separately passing the streams through the heater to heat the streams to a preset desired simulation temperature. The heated streams are then passed to a mixer where the streams are combined into a single process stream in which the simulated chemical reaction takes place. A pressure transducer and a backpressure valve/controller at the downstream end of the pressurized process stream maintains the preset desired pressure and flow rate of the process stream. The extent of reaction taking place in the process stream is measured. The formation of scale in the process stream causes pressure increase at the high pressure pumps due to constriction of flow in the process stream by the scale. Monitoring of the pressure differential between the high pressure pumps and the pressure transducer has been found to indicate scale formation very reliably. Another high pressure pump, capable of introducing material into the downstream end of the pressurized process stream before the backpressure valve, is used to halt or neutralize the scaling or corrosion reactions, by dilution and/or chemical addition to prevent scaling or precipitation in the back pressure valve. This high pressure pump is not necessarily programmable. After reduction in pressure and temperature, downstream of the backpressure valve, pH and chemical composition may be monitored, by analyses known to the art, and results may be fed to a computer for adjustment of the inputs to the simulation system. Each of the pressurized streams may be controlled by a computer analyzing desired preset and monitored conditions of temperature, pressure, pH, and chemical composition. A series of successive tests are conducted, each successively only reducing the concentration of the inhibitor, until the desired simulated chemical reaction is observed, such as scaling, from which the minimum effective concentration of inhibitor is ascertained. The apparatus and process of this invention have been found to be reliable and effective in the evaluation of inhibitors for prevention of $BaSO_4$ scaling with the concurrent scale formation of NORMs and is suitable for simulations at temperatures of about $-20°$ to about 150° C. and pressures up to about 5,000 psi.

BRIEF DESCRIPTION OF THE DRAWING

The above and further objects and advantages of the invention will become more apparent upon reading the detailed description together with reference to the drawing which is a simplified schematic showing of a high temperature/pressure dynamic inhibitor evaluation apparatus according to one embodiment of this invention.

DESCRIPTION OF PREFERRED EMBODIMENTS

Referring to the drawing as shown, high pressure pump 11 has the capability of mixing and supplying desired aqueous field simulated test solution containing an ionic concentration of one species of anions or cations required for conduct of the desired simulated chemical reaction and high pressure pump 12 has the capability of mixing and supplying desired aqueous field simulated test solution of an ionic concentration of the other species of anions or cations required for conduct of the desired simulated chemical reaction. In each case, the aqueous solution otherwise corresponds to the field composition of the aqueous system being simulated. At least one of these aqueous streams additionally initially contains at least sufficient concentration of chemical inhibitor being evaluated to inhibit the desired simulated chemical reaction. Pumps 11 and 12 have the capability of pressurizing the flow system to the desired simulation pressure, up to about 5000 psi. Suitable high pressure mixing pumps are commercially available, such as Eldex Laboratories, Inc., Pump Model 9600. The pressurized streams from pumps 11 and 12 are then passed separately through a temperature adjustment means, such as oil bath 14, which is capable of adjusting the temperature of the streams from pumps 11 and 12 to desired simulation temperature of $-20°$ up to about 150° C., following which the separate streams are passed to mixer 15 for mixing of the streams at the controlled elevated temperature and pressure to form a single process stream which accurately simulates the desired field conditions of temperature, pressure and chemical composition to allow the desired chemical reactions of scale formation, corrosion, inhibitor action, and the like to take place under simulated field conditions. High pressure pump 13 has the capability to add water and/or desired chemicals to the high temperature/pressure process stream upstream of back pressure valve/controller 17 before the process stream is cooled and returned to atmospheric pressure at valve/controller 17 after desired exposure of the process stream to desired simulated field conditions of scaling, corrosion, inhibitor action and the like. After cooling and return to atmospheric pressure, aliquots or side streams may then be passed to any desired measurement instrumentation for analysis of the process stream for specified components as determined by the type of testing being conducted. Shown in the figure is pH/Ion Sensitive Electrode 18 connected to pH/ISE meter 19 for pH measurement and flow through spectrophotometer 30 to which a side stream may be passed by valve 31 for desired chemical analysis. Cooled atmospheric pressure waste stream 32 drains from the apparatus.

The system is controlled by computer 20. Pressure transducer 16 monitors the high pressure in the process stream and transmits the information via communication line 26 to computer 20 which analyzes the measured pressure at the downstream end of the process stream together with the desired preset pressure and adjusts pump 11, pump 12 and valve/controller 17 through communication lines 21, 22 and 27, respectively, to obtain and maintain the desired pressure and flow rate in the process stream of the flow simulator system. When the desired simulated chemical reaction involves precipitation, such as scaling, the pressure differential between pumps 11 and 12 and pressure transducer 16 provides a measurement of the scaling since the formation of scale in the pressurized process stream causes increased pressure at pumps 11 and 12. The elevated temperature in the individual streams may also be monitored at the oil bath 14 and transmitted to computer 20. The measured temperatures together with the desired preset temperature of the process stream is monitored and the temperature of oil bath 14 adjusted to obtain and maintain the desired elevated temperature in the individual streams, and thus in the process stream, of the flow simulator system. Any suitable means for obtaining and maintaining the desired temperature of up to about 150° C. in the process stream, as will be well known in the art may be used. Computer 20 also may, but not necessarily, adjust the flow of dilution water and/or neutralizing chemical into the pressurized process stream prior to back pressure valve/controller 17 to prevent undesired scaling in backpressure valve/controller 17. A wide number of suitable computer, program and control systems for the apparatus and process of this invention will be apparent to one skilled in the art upon reading the above description.

An important feature of the flow simulator system of this invention is that the components of the system in contact with the chemical streams are entirely metal free to prevent sorption of chemicals onto the pump components and tubing. Suitable tubing and coating materials such as Teflon and polyetheretherketone (PEEK) may be used. It is important to eliminate sorption in the system to prevent "memory effects" from the same or previous evaluations from interfering with the current flow simulation.

The apparatus for evaluating inhibitor action in reduction of a specified chemical reaction under simulated field aqueous flow conditions, in accordance with this invention, has first pump means capable of forming a first aqueous stream corresponding to the pressure and chemical composition of said field aqueous flow except comprising a preset concentration of anions for said specified chemical reaction; second pump means capable of forming a second aqueous stream corresponding to the pressure and chemical composition of the field aqueous flow except comprising a preset concentration of cations for the specified chemical reaction; means for supplying preset decreasing concentrations of the inhibitor to at least one of the first and second pump means; first and second conduit means in fluid communication at their upstream end, respectively, with the aqueous stream outlet of the first and second pump means, the first and second conduit means passing in thermal transfer relation to temperature adjustment means capable of adjusting the temperature of the first and second aqueous streams to a preset temperature corresponding to the field aqueous flow conditions; mixing means in fluid communication with the downstream end of the first and second conduit means and capable of mixing the first and second aqueous streams to form a single process stream at pressure and temperature corresponding to the field aqueous flow conditions at its outlet; process stream conduit in fluid communication with the outlet of the mixing means for passage of the process stream; backpressure/controller valve means in fluid communication with the downstream end of the process stream conduit; pressure transducer means capable of measuring pressure in the process stream in fluid communication with the process stream conduit upstream of the backpressure/controller valve means, and computer means in signal communication for receiving signals from the pressure transducer means and receiving signals from, analyzing and controlling the first and second pump means and the backpressure/controller valve means.

The process according to this invention for evaluating an inhibitor chemical action reduction of a specified chemical reaction under simulated field flow conditions is achieved by: forming a first aqueous stream corresponding to the pressure and chemical composition of the aqueous field stream except comprising a preset concentration of anions for the specified chemical reaction; forming a second aqueous stream corresponding to the pressure and chemical composition of the aqueous field stream except comprising a preset concentration of cations for the specified chemical reaction; at least one of the first and second aqueous streams initially additionally comprising at least sufficient concentration of the inhibitor chemical being tested to inhibit the specified chemical reaction; separately adjusting the temperature of the first and second aqueous streams to a preset temperature corresponding to field conditions; mixing the first and second aqueous streams at pressure and temperature corresponding to field conditions being simulated; conducting a plurality of runs successively reducing the inhibitor concentration while maintaining the preset anion and cation concentration until detecting the specified chemical reaction. This will provide the minimum effective inhibitor concentration for the specific inhibitor being tested for the specified chemical reaction. It will be apparent to one skilled in the art that the described process may be modified to accommodate various field simulations being conducted.

With the capability of high temperature/pressure flow field simulation, accurate and reproducible results have been obtained with the apparatus and process of this invention for scale inhibitor evaluation for specific petroleum production fields. These results have been proven by field application and testing. The capability of providing separate streams of high pressure/temperature solutions prior to mixing make possible accurate and reproducible results involving BaSO$_4$ scaling and evaluation of inhibitors therefore.

Gas producers in the Michigan Basin, near Traverse City, Mich., have experienced scale due to CaCO$_3$ and BaSO$_4$ solids precipitation from water produced in conjunction with natural gas. Barite, BaSO$_4$, scale is a serious problem to the gas producing industry and has the potential to contain naturally occurring radioactive materials (NORM) which are currently an issue within regulatory bodies and more stringent regulations concerning NORM scales may result. By control of the scale problem, NORM and other scales being deposited in wells and surface equipment may be reduced or eliminated, thereby reducing or eliminating the NORM environmental risk and increasing gas production due to decrease of production loss due to equipment and/or facilities clogged with scale material.

Operators in the Michigan Basin reported that wells and production equipment were scaling with CaCO$_3$ and BaSO$_4$ and that the scale had coprecipitated NORM. Additionally, very high sulfate concentrations had been observed in some wells to be in excess of 4000 ppm, even though typical concentrations were undetectable by conventional methods. Water sampling taken at 133 Michigan Basin locations, including 108 well sites with the remainder being duplications, surface facilities and disposal wells, showed total dissolved solids in these wells ranged from about 25,000 to over 180,000 mg/l. Barium concentrations ranged from less than 1 mg/l to 185 mg/l with an average of 43 mg/l. Sulfate concentrations were measured at between less than about 3 mg/l, the detection limit, to 3233 mg/l with an average of 284 mg/l, in cases where sulfate was detected. The average values, however, can be misleading since that when sulfate was detected the barium concentration was generally low, and vice versa. Measurement of BaSO$_4$ solubilities and ionic strength of solutions from wells of the Michigan Basin studied indicate that the wells sampled were at equilibrium with barite in the reservoir. Some wells had produced NORM scale in the tubing due to higher sulfate levels in the produced brine. Scaling problems were most severe in wells where both sulfate and barium levels were detected.

Saturation index calculations, explained more fully in J. E. Oddo and M. B. Tomson, Why Scale Forms in the Oil Field and Methods to Predict It (Title changed for publication to Improvement on the Oddo-Tomson Saturation Indices for the Prediction of Common Oil Field Scales), J. Petr. Eng., in press (1993) which is incorporated herein by reference in its entirety, with respect to CaCO$_3$ indicated that all the wells considered had a tendency to produce CaCO$_3$ scale and while undersaturated with respect to gypsum, CaSO$_4$ scale would be expected under production conditions. The high sulfate wells were found to be much less undersaturated with respect to gypsum than wells with low sulfate which indicates that waters in these wells may be migrating from another formation having higher gypsum and/or other sulfate minerals. Consideration of normalized sulfate divided by calcium versus normalized chloride suggests that while some of the waters are approaching equilibrium with calcium sulfate most of the waters are very much undersaturated with calcium sulfate. Radiation readings taken at the sampling sites indicate that NORM scaling is primarily taking place in the handling facilities after commingling of the waters, but some wellheads exhibited small amounts of radioactivity which correlated well with BaSO$_4$ predictions from water chemistry. Radiation was also detected in the input flow lines to the separators indicating NORM scale forming upstream of the main surface facilities.

Scale inhibitor evaluations for the above described Michigan Basin wells was undertaken in the laboratory using the high temperature/pressure simulation apparatus as described above. The Michigan reservoirs are very shallow, about 1000 to 1600 feet, and are at about 70° F. and 100 psi. The composition of the brine used in the laboratory evaluations, having 45,140 mg/l Total Dissolved Solids and Ionic Strength of 0.85M, was as shown in Table 1.

TABLE 1

| Chemical Species | Concentration (mg/l) |
|---|---|
| Ba | 30 |
| Ca | 880 |
| Mg | 680 |
| HCO$_3$ | 150 |
| Cl | 27,000 |
| SO$_4$ | 1,100 |

Scale inhibitors evaluated for sulfate scale inhibition in the above brine were tested in the elevated temperature/pressure flow simulator as shown in the figure. For each scale inhibitor, the temperature and pressure of the apparatus were adjusted to the desired points for field simulation. The process stream flow was started with anions and cations being individually introduced by the pumps at a rate such that the combined stream had the simulated concentration of the actual oil or gas field water under consideration. The cation aqueous solution had sufficient scale inhibitor so that no scale formed in the system. When the apparatus reached equilibrium, the inhibitor in the cation stream was incrementally decreased in successive tests in a manner such that the combined stream had the identical concentrations of cations and anions, but only the amount of scale inhibitor was incrementally decreased. At some point, scale formed in the system due to the decreasing concentration of scale inhibitor and was detected by the change in pressure at the pumps as described above. At this point, the minimum effective dose or concentration required to inhibit scale for the scale inhibitor being tested under the test conditions is known. This results in a field applicable minimum concentration to inhibit scale and a ranking of the inhibitors being tested. Since the concentration of inhibitors being tested is a minimum effective dose, significant cost savings are realized in chemical treatment using correct concentrations and not treating with an excessive amount of chemical.

Eight generic threshold inhibitors were evaluated by this method and the results are shown in Table 2. Active concentrations refer to active concentrations of the inhibitor chemical in an aqueous solution. Minimum concentration refers to the lowest concentration that was effective for inhibition under conditions of the laboratory evaluations at 70° F. and 100 psi. Two values separated by a backslash indicate two runs to verify reproducibility.

TABLE 2

| Scale Inhibitor | Product Conc. (mg/l) | Active Conc. (%) | Min. Active Conc. (mg/l) |
| --- | --- | --- | --- |
| Phosphinopolycarboxylate A | 1.0/1.0 | 50 | 0.56/0.51 |
| Phosphinopolycarboxylate B | 1.3/1.2 | 42.5 | 0.56/0.51 |
| TEA Phosphate Ester | 3.8 | 32.7 | 1.2 |
| Polyacrylate | 6.8 | 34 | 2.3 |
| Phosphonate/Polymer Blend | 7.0 | 45 | 3.2 |
| Diethylenetriaminepenta (methylene phosphonic) Acid | 10.0 | 41.2 | 4.1 |
| Phosphonate A | >20.0/>20.0 | 38.5 | >7.7/>7.7 |
| Aminotrimethylene phosphonate | >20.0 | 42 | >8.4 |

The most effective scale inhibitor against $BaSO_4$ tested was phosphinopolycarboxylate (PPPC). The above tests have been described in J. E. Oddo, C. Stiz, I. Ortiz, D. Linz, A. Lawrence, A. T. Kan and M. B. Tomson, Naturally Occurring Radioactive Materials (NORM) Scale Formation—A Case Study of the Chemistry, Prediction, Remediation and Treatment in Wells of the Antrim Gas Fields Near Gaylord, Mich., SPE/EPA Exploration and Production Environmental Conference, San Antonio, Tex., Mar. 7-10, 1993, which is incorporated herein by reference in its entirety. The effectiveness of this inhibitor at the about the above minimum active concentration has been confirmed in the field by squeezing ten wells with no further scale detected in these wells.

Scale inhibitor evaluations were conducted in the same manner as described above at 194° F. and 250 psi for $FeCO_3$ scaling using aqueous solutions of the composition shown in Table 3.

TABLE 3

| Chemical Species | Concentration (mg/l) |
| --- | --- |
| Cl | 12,000 |
| $HCO_3$ | 16,000 |
| $SO_4$ | 1,150 |
| $Fe^{+2}$ | 600 |

The scale inhibitors evaluated by this method and the results are shown in Table 4.

TABLE 4

| Scale Inhibitor | Min. Active Conc. (mg/l) |
| --- | --- |
| Aminotrimethylene phosphoric acid | 2.5 |
| Phosphinopolycarboxylic acid | 15 |

The measurement of $FeCO_3$ scaling could not have been accomplished using prior methods of detection by pH change since $FeCO_3$ formation does not change the pH of the aqueous solution used.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

We claim:

1. A process for evaluating inhibitor action in reduction of a specified chemical reaction by simulating a field aqueous flow having known parameters, comprising: (A) forming a first aqueous stream having parameters corresponding to the pressure and chemical composition of said field aqueous flow except comprising a preset concentration of anions for said specified chemical reaction; (B) forming a second aqueous stream having parameters corresponding to the pressure and chemical composition of said field aqueous flow except comprising a preset concentration of cations for said specified chemical reaction, at least one of said first and second aqueous streams initially additionally comprising at least sufficient concentration of said inhibitor to inhibit said specified chemical reaction; (C) separately adjusting the temperature of said first and second aqueous streams to a preset temperature corresponding to that of said field aqueous flow; (D) mixing said first and second aqueous streams at said pressure and said temperature to form a single process stream; and (E) repeating said steps (A) through (D) successively reducing said inhibitor concentration while maintaining said preset concentration of anions in said first aqueous stream and said preset concentration of cations in said second aqueous stream until detecting said specified chemical reaction in said process stream.

2. A process for evaluating inhibitor action in accordance with claim 1 wherein said pressure is up to about 5000 psi.

3. A process for evaluating inhibitor action in accordance with claim 1 wherein said preset temperature is about −20° to about 150° C.

4. A process for evaluating inhibitor action in accordance with claim 1 wherein said pressure in said process stream is maintained by a backpressure/controller valve at the downstream end of said process stream, said backpressure/controller valve having means to control a backpressure upstream from said valve.

5. A process for evaluating inhibitor action in accordance with claim 4 wherein the pressure of said process stream upstream of said backpressure/controller valve is measured by a pressure transducer transmitting a signal of measured pressure to a computer which compares said signal corresponding to said pressure of said process stream with signals corresponding to pressure of said first and second aqueous streams and maintains constant pressure in said process stream by adjusting said backpressure/controller valve.

6. A process for evaluating inhibitor action in accordance with claim 4 additionally injecting diluting solution or chemical into said process stream just upstream of said backpressure/controller valve to prevent occurrence of said specified chemical reaction in said backpressure/controller valve.

7. A process for evaluating inhibitor action in accordance with claim 1 wherein said specified chemical reaction is formation of chemical salt scaling and said detecting is achieved by appearance of a pressure differential between said pressure in said first and second aqueous streams and pressure measured by a pressure transducer in said process stream.

8. A process for evaluating inhibitor action in accordance with claim 1 wherein said specified chemical reaction is chemical salt formation scaling, said chemical salt selected from the group consisting of $BaSO_4$, $FeCO_3$, $SrSO_4$, $CaSO_4$ and $CaCO_3$.

9. An apparatus adapted for adapted evaluating inhibitor action in reduction of a specified chemical reaction by simulating a field aqueous flow having known parameters, comprising: first pump means for forming a first aqueous stream having parameters to the pressure and chemical composition of said field aqueous flow except comprising a preset concentration of anions for said specified chemical reaction; second pump means for forming a second aqueous stream having parameters to the pressure and chemical composition of said field aqueous flow except comprising a preset concentration of cations for said specified chemical reaction; means for supplying preset decreasing concentrations of said inhibitor to at least one of said first and second pump means; first and second conduit means in fluid communication at their upstream ends, respectively, with the aqueous streams formed by said first and second pump means, said first and second conduit means passing in heat exchange relation to temperature adjustment means for adjusting the temperature of said first and second aqueous streams to a preset temperature corresponding to that of said field aqueous flow; mixing means in fluid communication with the downstream end of each of said first and second conduit means and for mixing said first and second aqueous streams to form a single process stream at said respective pressure and temperature corresponding to that of said field aqueous flow in the process stream; process stream conduit in fluid communication with said outlet of said mixing means for passage of said process stream; backpressure/controller valve means in fluid communication with said process stream conduit, said backpressure/controller valve having means to control a backpressure upstream from said valve; pressure transducer means for measuring pressure in said process stream in fluid communication with said process stream conduit upstream of said backpressure/controller valve means; and computer means in signal communication for receiving signals from said pressure transducer means and receiving signals from, analyzing and controlling said first and second pump means and said backpressure/controller valve means.

10. An apparatus for evaluating inhibitor action in accordance with claim 9 additionally comprising injection pump means capable of injecting diluting solution or chemical into said process stream conduit just upstream from said backpressure/controller valve means.

11. An apparatus for evaluating inhibitor action in accordance with claim 9 wherein said first pump means, second pump means and said backpressure/controller valve means are capable of maintaining pressure of up to about 5000 psi in streams in said first and second aqueous streams and said process stream conduit.

12. An apparatus for evaluating inhibitor action in accordance with claim 9 whereing said temperature adjustment means is capable of maintaining said preset temperature at about −20° to about 150° C.

13. A process for evaluating inhibitor action in reduction of $BaSO_4$ scale formation by simulating a field aqueous flow having known parameters, comprising: (A) forming a first aqueous stream having parameters corresponding to the pressure and chemical composition of said field aqueous flow except comprising a preset concentration of $SO_4$ anions for formation of said $BaSO_4$; (B) forming a second aqueous stream having parameters corresponding to the pressure and chemical composition of said field aqueous flow except comprising a preset concentration of Ba cations for formation of said $BaSO_4$, at least one of said first and second aqueous streams initially additionally comprising at least sufficient concentration of said inhibitor to inhibit formation of said $BaSO_4$; (C) separately adjusting the temperature of said first and second aqueous streams to a preset temperature corresponding to that of said field aqueous flow; (D) mixing said first and second aqueous streams at said pressure and said temperature to form a single process stream; and (E) repeating said steps (a) through (D) successively reducing said inhibitor concentration while maintaining said preset concentration of $SO_4$ anions in said first aqueous stream and said preset concentration of Ba cations in said second aqueous stream until detecting said $BaSO_4$ scale formation in said process stream.

14. A process for evaluating inhibitor action in accordance with claim 13 wherein said pressure in said process stream is maintained by a backpressure/controller valve at the downstream end of said process stream, said backpressure/controller valve having means to control a backpressure upstream from said valve.

15. A process for evaluating inhibitor action in accordance with claim 14 wherein the pressure of said process stream upstream of said backpressure/controller valve is measured by a pressure transducer transmitting a signal of that measured pressure to a computer which compares said signal corresponding to said pressure in said process stream with signals corresponding to pressure of said first and second aqueous streams and maintains constant pressure in said process stream by adjusting said backpressure/controller valve.

16. A process for evaluating inhibitor action in accordance with claim 14 comprising additionally injecting diluting solution or chemical into said process stream just upstream of said backpressure/controller valve to prevent occurrence of said $BaSO_4$ formation in said backpressure/controller valve, 17. A process for evaluating inhibitor action in accordance with claim 13 wherein said $BaSO_4$ formation scaling detecting is achieved by appearance of a pressure differential between said pressure in said first and second aqueous streams and pressure measured by a pressure transducer in said process stream.

* * * * *

UNITED STATES PATENT AND TRADEMARK OFFICE
CERTIFICATE OF CORRECTION

PATENT NO. : 5,370,799

DATED : December 6, 1994

INVENTOR(S) : John E. Oddo et al

It is certified that error appears in the above-indentified patent and that said Letters Patent is hereby corrected as shown below:

Column 10, line 63, claim 9, after "for" delete "adapted".

Column 10, line 67, claim 9, after "parameters" insert ---corresponding---.

Column 11, line 5, claim 9, before "to" insert ---corresponding---.

Signed and Sealed this

Eleventh Day of April, 1995

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,370,799

DATED : December 6, 1994

INVENTOR(S) : John E. Offo et al.

It is certified that error appears in the above-indentified patent and that said Letters Patent is hereby corrected as shown below:

Column 10, claim 9, line 63, after "for" delete "adapted".

Column 10, claim 9, line 67, after "parameters" insert --corresponding--.

Column 11, claim 9, line 5, before "to" insert --corresponding--.

Column 11, claim 9, line 11, delete "streams" and insert --stream--.

Column 11, claim 9, line 18, after "means" delete "and".

Column 12, claim 15, line 35, delete "that".

Signed and Sealed this

Fifteenth Day of August, 1995

Attest:

BRUCE LEHMAN

*Attesting Officer*   *Commissioner of Patents and Trademarks*